United States Patent
Wan et al.

(10) Patent No.: US 11,034,360 B2
(45) Date of Patent: Jun. 15, 2021

(54) METHOD AND APPARATUS THAT ADDRESS MOTION SICKNESS

(71) Applicant: GM GLOBAL TECHNOLOGY OPERATIONS LLC, Detroit, MI (US)

(72) Inventors: Jingyan Wan, Sterling Heights, MI (US); Omer Tsimhoni, Bloomfield Hills, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 0 days.

(21) Appl. No.: 16/157,553

(22) Filed: Oct. 11, 2018

(65) Prior Publication Data
US 2020/0114929 A1    Apr. 16, 2020

(51) Int. Cl.
*B60W 50/00*    (2006.01)
*A61M 21/02*    (2006.01)
(Continued)

(52) U.S. Cl.
CPC ....... *B60W 50/0098* (2013.01); *A61B 5/0077* (2013.01); *A61B 5/02055* (2013.01);
(Continued)

(58) Field of Classification Search
CPC ......... B60W 50/0098; B60W 2510/20; B60W 2520/105; B60W 2520/10;
(Continued)

(56) References Cited

U.S. PATENT DOCUMENTS 10,112,623 B2 * 10/2018 Sweeney .............. B60N 2/0244
10,482,669 B2 * 11/2019 Rober ................... B60W 10/04
(Continued)

FOREIGN PATENT DOCUMENTS

| JP | 2008230575 A | * 10/2008 | ........... A61M 21/02 |
| KR | 20160070617 A | * 6/2016 | |
| KR | 20170064909 A | * 6/2017 | |

OTHER PUBLICATIONS

English_Translation_KR20170064909A (Year: 2017).*
English_Translation_JP2008230575 (Year: 2008).*
English_Translation_KR20160070617A (Year: 2016).*

*Primary Examiner* — Peter D Nolan
*Assistant Examiner* — Ashley L Redhead, Jr.
(74) *Attorney, Agent, or Firm* — Lorenz & Kopf, LLP

(57) ABSTRACT

A method and apparatus that address motion sickness are provided. The method includes receiving rider profile information, trip information, environmental information and vehicle dynamics information, determining a probability that a rider will suffer from motion sickness during a ride based on the rider profile information, the trip information, the environmental information and the vehicle dynamics information, in response to the probability being greater than a predetermined threshold probability corresponding to a rider, performing motion sickness mitigation functions, and in response to the probability being less than the predetermined threshold probability corresponding to the rider, monitoring the rider to detect rider response information indicating whether the rider will suffer from motion sickness during the ride.

17 Claims, 3 Drawing Sheets

(51) Int. Cl.
*B60Q 9/00* (2006.01)
*G01C 21/34* (2006.01)
*A61B 5/0205* (2006.01)
*A61B 5/00* (2006.01)
*G16H 50/20* (2018.01)
*A61B 5/021* (2006.01)
*A61B 5/024* (2006.01)
*A61B 5/08* (2006.01)
*A61B 5/0533* (2021.01)
*A61M 21/00* (2006.01)

(52) U.S. Cl.
CPC .......... *A61B 5/6893* (2013.01); *A61B 5/6898* (2013.01); *A61B 5/7275* (2013.01); *A61B 5/7435* (2013.01); *A61B 5/7475* (2013.01); *A61M 21/02* (2013.01); *B60Q 9/00* (2013.01); *G01C 21/3415* (2013.01); *G01C 21/3461* (2013.01); *G01C 21/3484* (2013.01); *G16H 50/20* (2018.01); *A61B 5/021* (2013.01); *A61B 5/024* (2013.01); *A61B 5/0533* (2013.01); *A61B 5/0816* (2013.01); *A61B 2560/0252* (2013.01); *A61B 2562/029* (2013.01); *A61M 2021/005* (2013.01); *A61M 2021/0022* (2013.01); *A61M 2021/0027* (2013.01); *A61M 2205/3303* (2013.01); *B60W 2510/20* (2013.01); *B60W 2510/22* (2013.01); *B60W 2520/10* (2013.01); *B60W 2520/105* (2013.01); *B60W 2520/125* (2013.01); *B60W 2540/22* (2013.01); *B60W 2554/00* (2020.02); *B60W 2555/20* (2020.02)

(58) Field of Classification Search
CPC ....... B60W 2510/22; B60W 2520/125; B60W 2550/12; B60W 2550/20; B60W 2540/22; B60Q 9/00; A61B 5/6898; A61B 5/0077; A61B 5/02055; A61B 5/7275; A61B 5/7475; A61B 5/7435; A61B 5/6893; A61B 5/021; A61B 5/0816; A61B 2562/029; A61B 2560/0252; A61B 5/0245; A61B 5/0533; G01C 21/3415; G01C 21/3484; G01C 21/3461; A61M 21/02; A61M 2021/0027; A61M 2021/0022; A61M 2021/005; A61M 2205/3303; G16H 50/20
See application file for complete search history.

(56) References Cited

U.S. PATENT DOCUMENTS

| 2011/0130956 A1* | 6/2011 | Tracton | G01C 21/3644 |
| | | | 701/533 |
| 2017/0267253 A1* | 9/2017 | Schmidt | B60W 50/0097 |
| 2018/0052000 A1* | 2/2018 | Larner | G01C 21/3484 |

* cited by examiner

METHOD AND APPARATUS THAT ADDRESS MOTION SICKNESS

INTRODUCTION

Apparatuses and methods consistent with exemplary embodiments relate to motion sickness. More particularly, apparatuses and methods consistent with exemplary embodiments relate to detecting and addressing motion sickness in the context of a vehicle.

SUMMARY

One or more exemplary embodiments provide a method and an apparatus that address or mitigate motion sickness based on information provided by a mobile device and vehicle sensors. More particularly, one or more exemplary embodiments provide a method and an apparatus that determine the probability that motion sickness will occur based on rider profile information, trip information, environmental information and vehicle dynamics information and that mitigate or address motion sickness when the probability is above a predetermined threshold.

According to an aspect of exemplary embodiment, a method that addresses motion sickness is provided. The method includes receiving rider profile information, trip information, environmental information and vehicle dynamics information, determining a probability that a rider will suffer from motion sickness during a ride based on the rider profile information, the trip information, the environmental information and the vehicle dynamics information, in response to the probability being greater than a predetermined threshold probability corresponding to a rider, performing motion sickness mitigation functions; and in response to the probability being less than the predetermined threshold probability corresponding to the rider, monitoring the rider to detect rider response information indicating whether the rider will suffer from motion sickness during the ride.

The monitoring the rider to determine whether the rider suffers from motion sickness during the ride may include receiving the rider response information from one or more from among a camera, a microphone, a biometric sensor, and a user input device.

The method may also include updating the determined probability that the rider will suffer from motion sickness during the ride based on the rider response information, and in response to the updated probability being greater than the predetermined threshold probability corresponding to the rider, performing motion sickness mitigation functions.

The biometric sensors may include one or more from among a galvanic skin response sensor, a heart rate sensor, a respiration rate sensor, a skin temperature sensor, blood pressure sensor, and an infrared sensor, the camera may include one or more from among an in vehicle camera, an infrared camera, and a mobile device camera, the microphone may include one or more from among a microphone embedded in a vehicle and a microphone of a mobile device, and the user input device may include one or more from among a touch screen, a button, a keyboard, and a dial.

The rider profile information may include one or more from among demographic information, health condition information, sleep information, meal information, motion sickness history information of rider, motion sickness history information of other riders.

The trip information may include one or more from among a trip start time, a trip end time, traffic information, weather conditions, trip duration, trip distance, route elevation changes, route stops, and turns on a route.

The vehicle dynamics information may include one or more from among lateral acceleration, longitudinal acceleration, speed, steering information, suspension settings, seat position, and seat orientation.

The environmental information may include one or more from among temperature information, humidity information, airflow information, window position information, ambient light information, and odor information.

The determining the probability that the rider suffers from motion sickness may be performed based on conditional functions corresponding to ride duration, each of the conditional functions may comprise a sum of a constant for the ride duration corresponding to the conditional function and a product of one or more functions, and the one or more functions may include a first function of the rider profile information, the environmental information, the trip information and the vehicle dynamics information, a second function of rider response information, a third function corresponding to a sum of vehicle motion, and a fourth function corresponding to a sum of rider head motion.

The performing motion sickness mitigation functions may include one or more from among adjusting environmental conditions in a vehicle, outputting displayed images, lights, text, auditory or tactile information configured to assist the rider in mitigating motion sickness, controlling vehicle movement to address motion sickness, providing access to motion sickness medication and remedies, and adjusting a route of a vehicle to address motion sickness.

According to an aspect of an exemplary embodiment, an apparatus that addresses motion sickness is provided. The apparatus includes: at least one memory comprising computer executable instructions; and at least one processor configured to read and execute the computer executable instructions. The computer executable instructions cause the at least one processor to receive rider profile information, trip information, environmental information and vehicle dynamics information, determine a probability that a rider will suffer from motion sickness during a ride based on the rider profile information, the trip information, the environmental information and the vehicle dynamics information, in response to the probability being greater than a predetermined threshold probability corresponding to a rider, perform motion sickness mitigation functions, and in response to the probability being less than the predetermined threshold probability corresponding to the rider, monitoring the rider to detect rider response information indicating whether the rider will suffer from motion sickness during the ride.

The computer executable instructions may cause the at least one processor to monitor the rider to determine whether the rider suffers from motion sickness during the ride by receiving the rider response information from one or more from among a camera, a microphone, a biometric sensor, and a user input device.

The computer executable instructions may cause the at least one processor to update the rider profile or the determined probability that the rider will suffer from motion sickness during the ride based on the rider response information, and in response to the updated probability being greater than the predetermined threshold probability corresponding to the rider, perform motion sickness mitigation functions.

The biometric sensors may include one or more from among a galvanic skin response sensor, a heart rate sensor, a respiration rate sensor, a skin temperature sensor, blood pressure sensor, and an infrared sensor, the camera may include one or more from among an in vehicle camera, an infrared camera, and a mobile device camera, the microphone may include one or more from among a microphone embedded in a vehicle and a microphone of a mobile device, and the user input device may include one or more from among a touch screen, a button, a keyboard, and a dial.

The rider profile information may include one or more from among demographic information, health condition information, sleep information, meal information, motion sickness history information of rider, motion sickness history information of other riders.

The trip information may include one or more from among a trip start time, a trip end time, traffic information, weather conditions, trip duration, trip distance, route elevation changes, route stops, and turns on a route.

The vehicle dynamics information may include one or more from among lateral acceleration, longitudinal acceleration, steering information, suspension settings, seat position, and seat orientation.

The environmental information may include one or more from among temperature information, humidity information, airflow information, window position information, ambient light information, and odor information.

The computer executable instructions may cause the at least one processor to determine the probability that the rider suffers from motion sickness based on conditional functions corresponding to ride duration, each of the conditional functions may comprise a sum of a constant for the ride duration corresponding to the conditional function and a product of one or more functions, and the one or more functions may include a first function of the rider profile information, the environmental information, the trip information and the vehicle dynamics information, a second function of rider response information, a third function corresponding to a sum of vehicle motion, and a fourth function corresponding to a sum of rider head motion.

The computer executable instructions may cause the at least one processor to the perform motion sickness mitigation functions by performing one or more from among adjusting environmental conditions in a vehicle, outputting displayed images, lights, text, auditory or tactile information configured to assist the rider in mitigating motion sickness, controlling vehicle movement to address motion sickness, providing access to motion sickness medication and remedies, and adjusting a route of a vehicle to address motion sickness.

Other objects, advantages and novel features of the exemplary embodiments will become more apparent from the following detailed description of exemplary embodiments and the accompanying drawings.

DETAILED DESCRIPTION OF EXEMPLARY EMBODIMENTS

Figure 1:
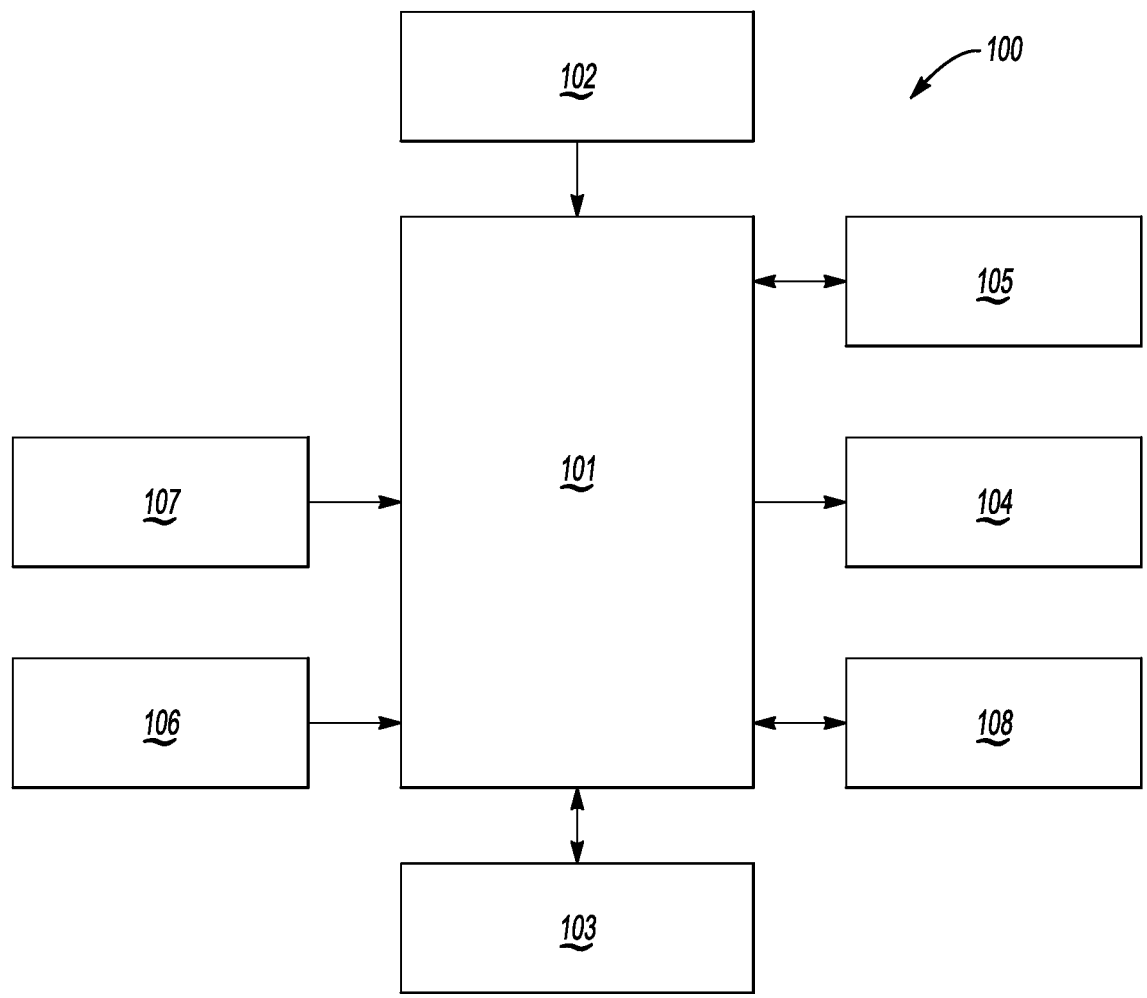
FIG. 1 shows a block diagram of an apparatus that addresses motion sickness according to an exemplary embodiment.

An apparatus and method that address motion sickness in a vehicle will now be described in detail with reference to FIGS. 1-3 of the accompanying drawings in which like reference numerals refer to like elements throughout.

The following disclosure will enable one skilled in the art to practice the inventive concept. However, the exemplary embodiments disclosed herein are merely exemplary and do not limit the inventive concept to exemplary embodiments described herein. Moreover, descriptions of features or aspects of each exemplary embodiment should typically be considered as available for aspects of other exemplary embodiments.

It is also understood that where it is stated herein that a first element is "connected to," "attached to," "formed on," or "disposed on" a second element, the first element may be connected directly to, formed directly on or disposed directly on the second element or there may be intervening elements between the first element and the second element, unless it is stated that a first element is "directly" connected to, attached to, formed on, or disposed on the second element. In addition, if a first element is configured to "send" or "receive" information from a second element, the first element may send or receive the information directly to or from the second element, send or receive the information via a bus, send or receive the information via a network, or send or receive the information via intermediate elements, unless the first element is indicated to send or receive information "directly" to or from the second element.

Throughout the disclosure, one or more of the elements disclosed may be combined into a single device or into one or more devices. In addition, individual elements may be provided on separate devices.

As vehicles are being increasingly shared and with the spread of mobile smart devices, such as mobile phones, there is an opportunity to use information provided by mobile devices to customize or enhance an experience of a person entering a vehicle. Generally, vehicle settings and functions are configured to accommodate a majority or plurality of drivers, occupants or riders. With the increase in the availability of information about riders and occupants due to vehicles being equipped with sensors and systems that may be leveraged to collect the additional information, this additional information may be used to adjust vehicle settings and controls vehicles in manner to increase the ride comfort of an occupant of a vehicle.

In one such example, rider profile information, trip information, environmental information and vehicle dynamics information may be processed to determine a probability that an occupant or rider in a vehicle will become motion sick. Based on the determined probability, a controller may control various systems of the vehicle to address the potential for motion sickness. Moreover, the calculation of or the probability of motion sickness of a rider may be continuously updated during a ride to take into additional information in determining whether to perform motion sickness mitigation functions. Motion sickness mitigation functions may be performed to prevent or delay motion sickness. In addition, they may be performed prior to the rider entering a vehicle by preparing the vehicle for the rider. This may be especially helpful in the context of autonomous vehicles where susceptibility to motion sickness may vary from rider to rider.

FIG. 1 shows a block diagram of an apparatus that addresses motion sickness 100 according to an exemplary embodiment. As shown in FIG. 1, the apparatus that addresses motion sickness 100, according to an exemplary embodiment, includes a controller 101, a power supply 102, a storage 103, an output 104, vehicle settings and controls 105, a user input 106, a sensor 107 and a communication device 108. However, the apparatus that addresses motion sickness 100 is not limited to the aforementioned configuration and may be configured to include additional elements and/or omit one or more of the aforementioned elements. The apparatus that addresses motion sickness 100 may be implemented as part of a vehicle, as a standalone component, as a hybrid between an on vehicle and off vehicle device, or in another computing device.

The controller 101 controls the overall operation and function of the apparatus that addresses motion sickness 100. The controller 101 may control one or more of a storage 103, an output 104, vehicle settings and controls 105, a user input 106, a sensor 107 and a communication device 108 of the apparatus that addresses motion sickness 100. The controller 101 may include one or more from among a processor, a microprocessor, a central processing unit (CPU), a graphics processor, Application Specific Integrated Circuits (ASICs), Field-Programmable Gate Arrays (FPGAs), state machines, circuitry, and a combination of hardware, software and firmware components.

The controller 101 is configured to send and/or receive information from one or more of the storage 103, the output 104, the vehicle settings and controls 105, the user input 106, the sensor 107 and the communication device 108 of the apparatus that addresses motion sickness 100. The information may be sent and received via a bus or network, or may be directly read or written to/from one or more of the storage 103, the output 104, the vehicle settings and controls 105, the user input 106, the sensor 107 and the communication device 108 of the apparatus that addresses motion sickness 100. Examples of suitable network connections include a controller area network (CAN), a media oriented system transfer (MOST), a local interconnection network (LIN), a local area network (LAN), wireless networks such as Bluetooth and 802.11, and other appropriate connections such as Ethernet.

The power supply 102 provides power to one or more of the controller 101, the storage 103, the output 104, the vehicle settings and controls 105, the user input 106, the sensor 107 and the communication device 108, of the apparatus that addresses motion sickness 100. The power supply 102 may include one or more from among a battery, an outlet, a capacitor, a solar energy cell, a generator, a wind energy device, an alternator, etc.

The storage 103 is configured for storing information and retrieving information used by the apparatus that addresses motion sickness 100. The storage 103 may be controlled by the controller 101 to store and retrieve information including profile information, trip information, environmental information, rider response information, and vehicle dynamics. The information may be collected and received the from user input 106, the communication device 108 or from one or more of the sensors 107. The storage 103 may also include the computer instructions configured to be executed by a processor to perform the functions of the apparatus that addresses motion sickness 100.

The rider profile information may include one or more from among demographic information (e.g., age, weight), health condition information (e.g., information on an affliction that causes or increases susceptibility to motion sickness), sleep information (e.g., hours slept in a time period, quality of sleep), meal information (e.g., a time of the last meal, a type of food in the last meal), motion sickness history information of rider (e.g., a count of the times the rider has become motion sick, places where the rider has become motion sick, types of vehicle motion that cause the rider motion sickness, time to first sign of motion sickness, rider's first symptom of motion sickness), motion sickness history information of other riders (whether other riders with similar profiles as the rider have become motion sick on similar routes, susceptibility of other riders with similar profiles as the rider to motion sickness, etc.).

The trip information may include one or more from among a trip start time, a trip end time, traffic information of route, weather conditions, trip duration, trip distance, route elevation changes, route stops, and turns on a route.

The environmental information may include temperature information, humidity information, airflow information, window position information, ambient light information, and odor information.

The vehicle dynamics information may include one or more from among lateral acceleration, longitudinal acceleration, speed information, steering information, suspension settings, seat position, and seat orientation. The vehicle dynamics information may be provided by sensors 107 or reading information provided by the vehicle settings and controls 105.

The rider response information may include one or more from among captured images, recorded audio, and sensed biometric information. The images of the rider may be used to detect visual symptoms of motion sickness. The biometric information may include heart rate, respiration rate, skin temperature, blood pressure, or galvanic skin response and be used to detect physiological symptoms of motion sickness. The audio may include voice information such as spoken words or other sounds indicating motion sickness. Other examples of rider response information may include information on a gaze of a rider, head movement of a rider, yawning by a rider, or tasks performed by a rider such has operating window controls, climate controls, etc. In addition, the rider response information may also include information one or more from among blood pressure or change in blood pressure, respiration rate, heart rate, skin temperature, sweat, skin color tone change, etc.

The storage 103 may include one or more from among floppy diskettes, optical disks, CD-ROMs (Compact Disc-Read Only Memories), magneto-optical disks, ROMs (Read Only Memories), RAMs (Random Access Memories), EPROMs (Erasable Programmable Read Only Memories), EEPROMs (Electrically Erasable Programmable Read Only Memories), magnetic or optical cards, flash memory, cache memory, and other type of media/machine-readable medium suitable for storing machine-executable instructions.

The output 104 outputs information in one or more forms including: visual, audible and/or haptic form. The output 104 may be controlled by the controller 101 to provide outputs to the user of the apparatus that addresses motion sickness 100. The output 104 may include one or more from among a speaker, audio, a display, a centrally-located display, a head up display, a windshield display, a haptic feedback device, a vibration device, a tactile feedback device, a tap-feedback device, a holographic display, an instrument light, an indicator light, etc.

The output 104 may output notification including one or more from among an audible notification, a light notification, and a display notification. The notification may include information notifying of a value of a vehicle setting or notifying that a vehicle setting is being adjusted. In addition, the output 104 may display a message for a person at an appropriate location in the vehicle.

The output 104 may display images, graphics, text, or deliver directional auditory or tactile information that show both real-time and future acceleration, deceleration, jerk, direction, projecting motion flow. The output 104 may be in the vehicle and include one or more displays or a smart wearable device such as glasses. The output 104 may present moving images on the display to represent the vehicle motion, provide an image or live video of an area in front of a vehicle, notify the rider to rest head on head rest, output music to a limited zone close to head rest corresponding to a rider zone to guide the rider to rest head on head rest, present images instead of text for passengers who are sensitive to gaze fixation in moving environments, or notify riders looking outside to turn gaze inside of vehicle.

The vehicle settings and controls 105 may include vehicle system modules (VSMs) in the form of electronic hardware components that are located throughout the vehicle and typically receive input from one or more sensors and use the sensed input to perform diagnostic, monitoring, control, reporting and/or other functions. Each of the VSMs may be connected by a communications bus to the other VSMs, as well as to the controller 101, and can be programmed to run vehicle system and subsystem diagnostic tests. The controller 101 may be configured to send and receive information from the VSMs and to control VSMs to perform vehicle functions.

As examples, one VSM can be an engine control module (ECM) that controls various aspects of engine operation such as fuel ignition and ignition timing, another VSM can be an external sensor module configured to receive information from external sensors such as cameras, radars, LIDARs, and lasers, another VSM can be a powertrain control module that regulates operation of one or more components of the vehicle powertrain, another VSM can be the vehicle dynamics sensor that detects a steering wheel angle parameter, a speed parameter, an acceleration parameter, a lateral acceleration parameter, a self-aligning torque parameter and/or a power steering torque parameter, and another VSM can be a body control module that governs various electrical components located throughout the vehicle, like the vehicle's power door locks and headlights. According to an exemplary embodiment, the engine control module is equipped with on-board diagnostic (OBD) features that provide myriad real-time data, such as that received from various sensors including vehicle emissions sensors, and provide a standardized series of diagnostic trouble codes (DTCs) that allow a technician to rapidly identify and remedy malfunctions within the vehicle. As is appreciated by those skilled in the art, the above-mentioned VSMs are only examples of some of the modules that may be used in a vehicle, as numerous others are also available.

The user input 106 is configured to provide information and commands to the apparatus that addresses motion sickness 100. The user input 106 may be used to provide user inputs, etc., to the controller 101. The user input 106 may include one or more from among a touchscreen, a keyboard, a soft keypad, a button, a motion detector, a voice input detector, a microphone, a camera, a trackpad, a mouse, a touchpad, etc.

The user input 106 may be configured to receive a user input to acknowledge or dismiss the notification output by the output 104. The user input 106 may also be configured to receive a user input to adjust a vehicle setting. The adjusted vehicle setting may then be stored in storage 103.

The sensor 107 may include one or more sensors from a biometric sensor, a camera, a galvanic skin response sensor, a heart rate sensor, a respiration rate sensor, a blood pressure sensor, a skin temperature sensor, humidity sensor, temperature sensor, and an infrared sensor, an infrared thermal camera, an accelerometer, a barometer, an elevation sensor, a light sensor, an odor sensor, an altimeter, a speedometer, and a braking sensor. In one example, the camera may be one or more from among an in-vehicle camera, an infrared camera, and a mobile device camera. In another example, an odor sensor may be an electronic nose instrument trained with qualified samples to build a database of reference noises corresponding to odors. The instrument may recognize new samples by comparing a volatile compound's fingerprint to those contained in the database using a qualitative or quantitative analysis.

The microphone may be one or more from among a microphone embedded in a vehicle and a microphone of a mobile device.

The communication device 108 may be used by apparatus that addresses motion sickness 100 to communicate with several types of external apparatuses according to various communication methods. The communication device 108 may be used to send/receive information from a mobile device. The communication device 108 may send information and notifications to be output by the mobile device by an output at the mobile device that performs functions similar to output 104.

The communication device 108 may include various communication modules such as one or more from among a telematics unit, a broadcast receiving module, a near field communication (NFC) module, a GPS receiver, a wired communication module, or a wireless communication module. The broadcast receiving module may include a terrestrial broadcast receiving module including an antenna to receive a terrestrial broadcast signal, a demodulator, and an equalizer, etc. The NFC module is a module that communicates with an external apparatus located at a nearby distance according to an NFC method. The GPS receiver is a module that receives a GPS signal from a GPS satellite and detects a current location. The wired communication module may be a module that receives information over a wired network such as a local area network, a controller area network (CAN), or an external network. The wireless communication module is a module that is connected to an external network by using a wireless communication protocol such as IEEE 802.11 protocols, WiMAX, Wi-Fi or IEEE communication protocol and communicates with the external network. The wireless communication module may further include a mobile communication module that accesses a mobile communication network and performs communication according to various mobile communication standards such as $3^{rd}$ generation (3G), $3^{rd}$ generation partnership project (3GPP), long-term evolution (LTE), Bluetooth, EVDO, CDMA, GPRS, EDGE or ZigBee.

According to an exemplary embodiment, the controller 101 of the apparatus that addresses motion sickness 100 may be configured to receive rider profile information, trip information, environmental information and vehicle dynamics information, determine a probability that a rider will suffer from motion sickness during a ride based on the rider profile information, the trip information, the environmental information and the vehicle dynamics information, in response to the determined probability being greater than a predetermined threshold probability corresponding to a rider, perform motion sickness mitigation, delaying or prevention functions, and in response to the probability being less than the predetermined threshold probability corresponding to the rider, monitoring the rider to detect rider response information indicating whether the rider will suffer from motion sickness during the ride.

In one example, the motion sickness mitigation, delaying or prevention functions can be performed during the ride as well as before the ride starts. For example, the vehicle can set the cabin temperature lower in a warm day. Since the temperature change is slow, this function can be performed on the way to the rider.

The controller may transform the rider profile information, the environmental information, the trip information, the vehicle dynamics information, and the rider response information into matrices, numbers, etc., modeling how each piece of information affects the probability of motion sickness. The transformed information may then be input into functions that calculate the effect of the information on the probability that a rider will suffer from motion sickness. For example, the controller may transform information from a heart rate sensor about the current heart rate and heart rate variance into a model. The model may be compared to a personalized model or threshold.

The determining a probability that a rider will suffer from motion sickness during a ride may be performed according to one or more the conditional functions. The one or more functions may include a first function of the rider profile information, the environmental information, the trip information and the vehicle dynamics information, a second function of rider response information, a third function corresponding to a sum of vehicle motion, and a fourth function corresponding to a sum of rider head motion.

An example of a conditional function is:

$$P_{sickness} = \begin{cases} A + f(rp, ei, ti, vi) \times g(rri, t) \times \left(\sum V_m * t\right) \times \left(\sum H_m * t\right) \text{ if trip} < t_1 \\ B + h(rp, ei, ti, vi) \times k(rri, t) \times \left(\sum V_m * t\right) \times \left(\sum H_m * t\right) \text{ if trip} \geq t_1 \end{cases},$$

where A and B are constants, rp is rider profile information, ei is environmental information, ti is trip information, vi is vehicle dynamics information, $V_m$ is vehicle motion, Hm is head motion and t is time. The functions f( ), g( ), h( ), and k( ) may be linear, logistic regression or machine learning functions.

The predetermined threshold probability corresponding the rider may be a preset threshold probability corresponding to when to perform functions to mitigate or address motion sickness. The predetermined threshold probability may include a plurality of predetermined threshold probabilities the controller 101 may control to perform different or additional motion mitigation, delaying or prevention functions when the determined probability exceeds different or additional predetermined threshold probabilities from among the plurality of threshold probabilities.

In addition, the controller 101 of the apparatus that addresses motion sickness 100 may also be configured to monitor the rider to determine whether the rider suffers from motion sickness during the ride by receiving the rider response information from one or more from among a camera, a microphone, a biometric sensor, and a user input device.

Further, the controller 101 of the apparatus that addresses motion sickness 100 may be configured to update the driver profile or the determined probability that the rider will suffer from motion sickness during the ride based on the rider response information, and in response to the updated probability being greater than the predetermined threshold probability corresponding to the rider, perform motion sickness mitigation, delaying or prevention functions.

In addition, the controller 101 of the apparatus that addresses motion sickness 100 may be configured to control to perform motion sickness mitigation, delaying or prevention functions by performing one or more from among adjusting environmental conditions in a vehicle, outputting displayed images or lights configured to assist the rider in mitigating motion sickness, controlling vehicle movement so as to address, mitigate, prevent or delay motion sickness, providing access to motion sickness medication, and adjusting a route of a vehicle to address motion sickness.

The controller 101 may control output 104 to address motion sickness by outputting a displayed image, lights, text, auditory or tactile information configured to assist the rider in mitigating motion sickness, displaying images, graphics, text, or delivering directional auditory or tactile information that show both real-time and future acceleration, deceleration, jerk, direction. In addition, the controller 101 may control output 104 to address motion sickness by controlling to project motion flow in vehicle on one or more displays or a smart wearable device such as glasses, present moving images on the display to represent the vehicle motion, provide an image or live video of an area in front of a vehicle, notify the rider to rest head on head rest, output music to a limited zone close to the head rest corresponding to a rider zone, output instructions to guide the rider to rest head on head rest, present image instead of text for passengers who are sensitive to gaze fixation in moving environments, or notify riders looking outside to turn gaze inside of vehicle.

The controller 101 may control vehicle movement to address motion sickness by controlling to decrease the magnitude of acceleration, deceleration, jerk, roll, yaw, pitch, or vibration, and adjusting suspension of a vehicle or a seat to dampen vibration.

The adjusting a route of a vehicle to address motion sickness may include ending a trip early, adjusting a route to avoid traffic, stopping, turns, bumpy roads, and up and down roads.

The controller 101 may adjust environmental conditions in a vehicle by controlling to adjust climate controls such as temperature, humidity, or fan speed. In addition, adjusting environmental conditions may also include one or more from among filtering air in the vehicle, releasing aromas to provide aromatherapy, or playing music or videos.

The controller 101 may provide access to motion sickness medication, water or food by controlling to open a compartment with motion sickness medication, to spray motion sickness medication, or to dispense motion sickness medication. The medication may include a Scopolamine, Dramamine, water, low fat/odor snacks etc.

Figure 2:
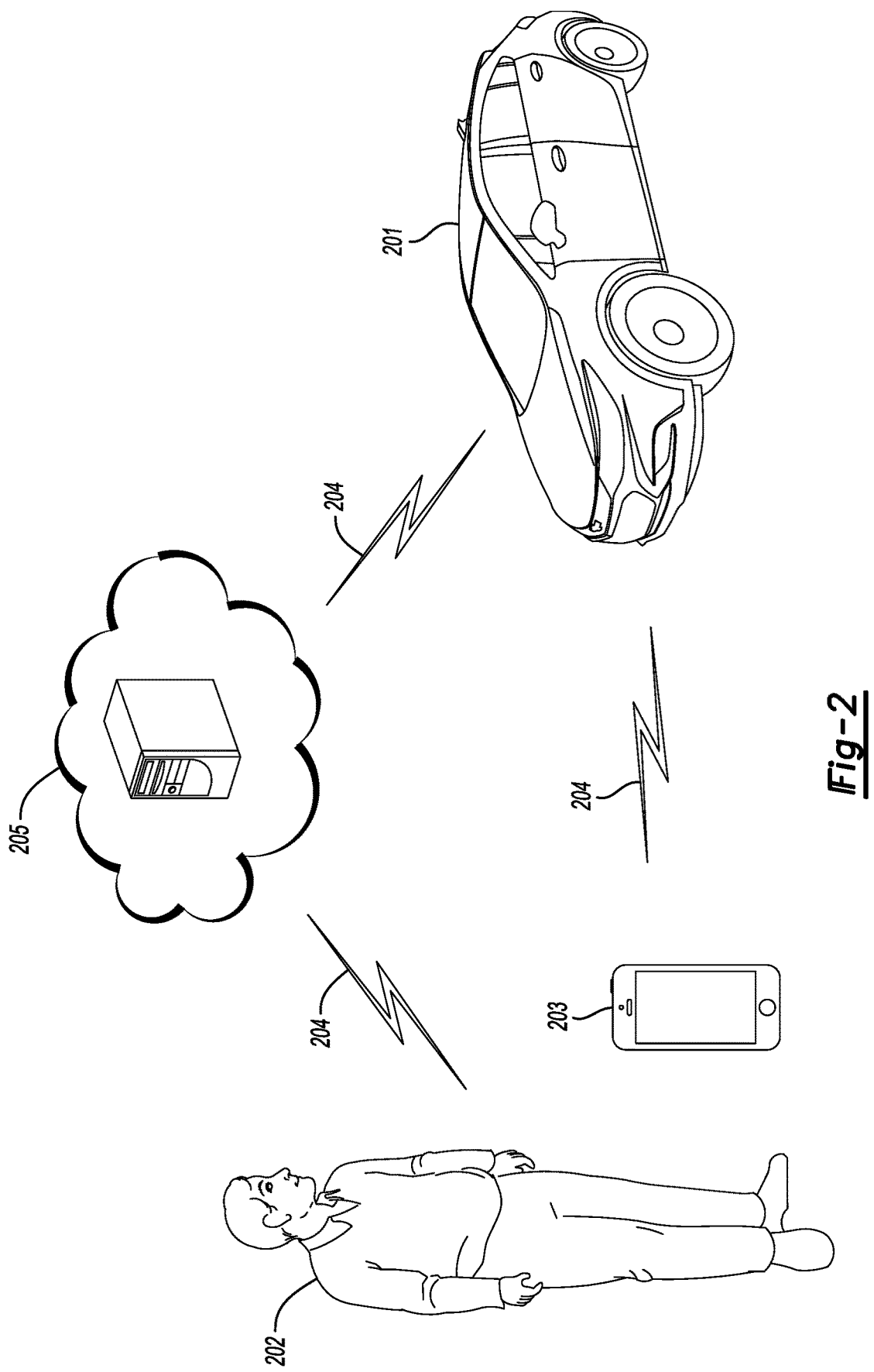
FIG. 2 shows an illustrative diagram of a system that addresses motion sickness according to an exemplary embodiment.

FIG. 2 shows an illustrative diagram of a system that addresses motion sickness according to an aspect of an exemplary embodiment. Referring to FIG. 2, a potential rider 202 or occupant may have a mobile device 203 such as smart phone or wearable smart device. As the rider 202 approaches or enters vehicle 201, information from sensors or storage in the mobile device 203 may be transmitted to vehicle 201 via wireless communication network 204. Moreover, information about the rider 202 may be stored or exchanged via server 205 in the cloud.

The vehicle 201 may include vehicle settings and controls 105 that are updated after determining the probability of motion sickness of the rider based on the information transmitted from the mobile device 203 as well as based on information from vehicle sensors 107 and the vehicle settings and controls 105, which may be integrated into the vehicle 201. After processing the information to determine the probability of a rider 202 becoming motion sick, the vehicle 201 may be controlled to perform the motion sickness mitigation, delaying, or prevention functions described above.

Figure 3:
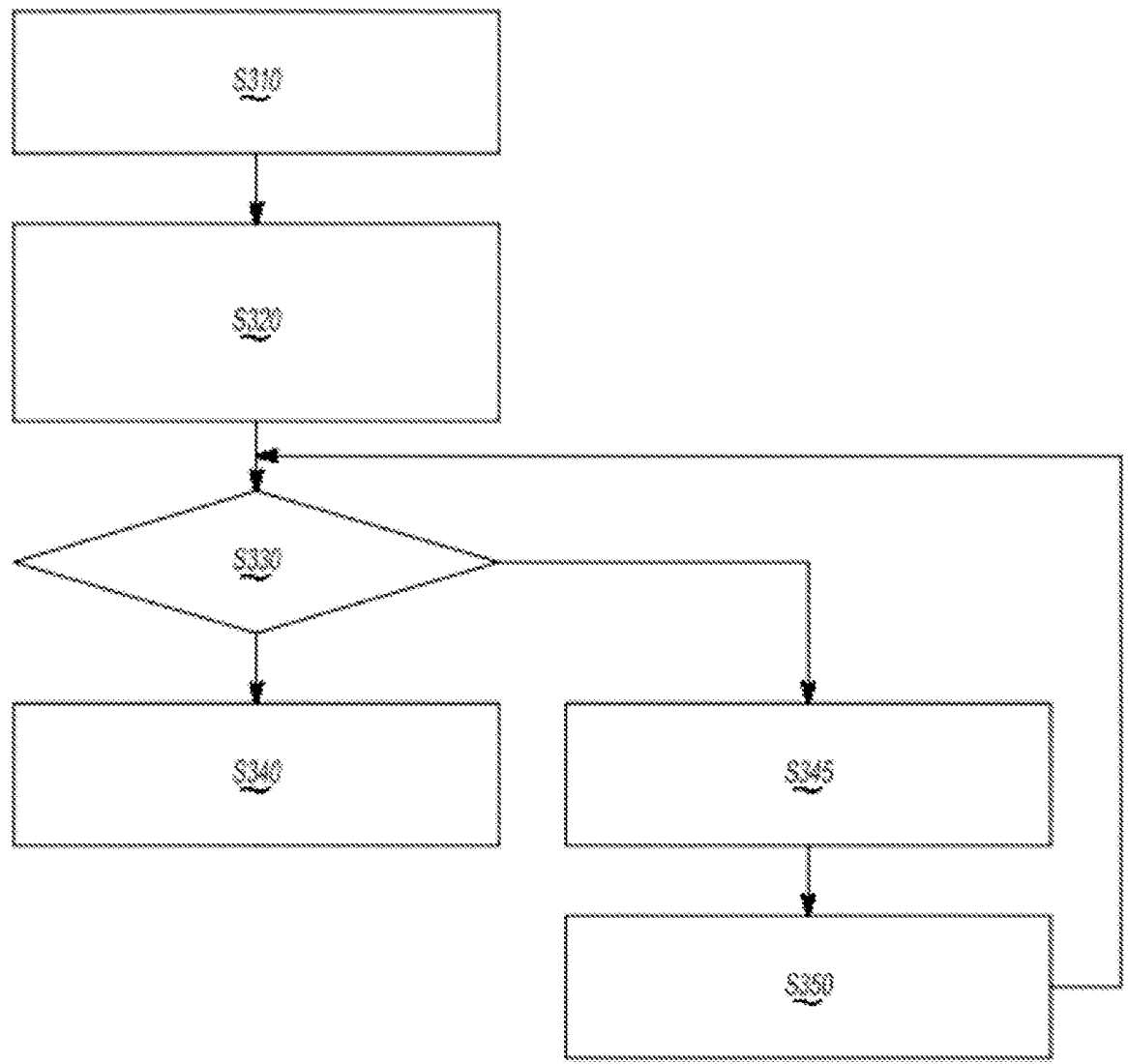
FIG. 3 shows a flowchart for a method addresses motion sickness according to an exemplary embodiment.

FIG. 3 shows a flowchart for a method that addresses motion sickness according to an exemplary embodiment. The method of FIG. 3 may be performed by the apparatus that addresses motion sickness 100 or may be encoded into a computer readable medium as instructions that are executable by a computer to perform the method.

Referring to FIG. 3, rider profile information, trip information, environmental information and vehicle dynamics information may be collected or received and process in operation S310. In operation S320, a probability that a rider will suffer from motion sickness during a ride is determined based on the rider profile information, the trip information, the environmental information and the vehicle dynamics information.

If the probability being greater than a predetermined threshold probability corresponding to a rider (operation S330-Yes), motion sickness mitigation, prevention, delaying functions are performed in operation S340.

If the probability being less than the predetermined threshold probability corresponding to a rider (operation S330-No), the rider is monitored to detect rider response information indicating whether the rider will suffer from motion sickness during the ride in operation S345. Then in operation S350, the rider profile and the determined probability of the rider suffering from motion sickness during ride are updated based on rider response information and the process returns to operation S330.

The processes, methods, or algorithms disclosed herein can be deliverable to/implemented by a processing device, controller, or computer, which can include any existing programmable electronic control device or dedicated electronic control device. Similarly, the processes, methods, or algorithms can be stored as data and instructions executable by a controller or computer in many forms including, but not limited to, information permanently stored on non-writable storage media such as ROM devices and information alterably stored on writeable storage media such as floppy disks, magnetic tapes, CDs, RAM devices, and other magnetic and optical media. The processes, methods, or algorithms can also be implemented in a software executable object. Alternatively, the processes, methods, or algorithms can be embodied in whole or in part using suitable hardware components, such as Application Specific Integrated Circuits (ASICs), Field-Programmable Gate Arrays (FPGAs), state machines, controllers or other hardware components or devices, or a combination of hardware, software and firmware components.

One or more exemplary embodiments have been described above with reference to the drawings. The exemplary embodiments described above should be considered in a descriptive sense only and not for purposes of limitation. Moreover, the exemplary embodiments may be modified without departing from the spirit and scope of the inventive concept, which is defined by the following claims.

What is claimed is:

1. A method that addresses motion sickness, the method comprising:
   receiving rider profile information, trip information, environmental information and vehicle dynamics information wherein the rider profile information includes motion sickness history information of a rider;
   determining a probability that the rider will suffer from motion sickness during a ride based on the rider profile information, the trip information, the environmental information and the vehicle dynamics information, wherein the motion sickness history information of the rider includes at least one of a count of the times the rider has become motion sick, places where the rider has become motion sick, types of vehicle motion that cause the rider motion sickness, time to first sign of motion sickness, rider's first symptom of motion sickness;
   in response to the probability being greater than a predetermined threshold probability corresponding to a rider, adjusting a route to generate an adjusted route to reduce the probability wherein the route is determined in response to the trip information; and
   controlling vehicle movement along the adjusted route.

2. The method of claim 1, further comprising monitoring the rider to determine whether the rider suffers from motion sickness during the ride comprises receiving the rider response information from one or more from among a camera, a microphone, a biometric sensor, and a user input device.

3. The method of claim 2, further comprising updating the rider profile or the determined probability that the rider will suffer from motion sickness during the ride based on the rider response information; and
   in response to the updated probability being greater than the predetermined threshold probability corresponding to the rider, performing motion sickness mitigation functions.

4. The method of claim 3, wherein the biometric sensors comprise one or more from among a galvanic skin response sensor, a heart rate sensor, a respiration rate sensor, a skin temperature sensor, blood pressure sensor, and an infrared sensor, wherein the camera comprises one or more from among an in vehicle camera, an infrared camera, and a mobile device camera, wherein the microphone comprises one or more from among a microphone embedded in a vehicle and a microphone of a mobile device, and wherein the user input device comprises one or more from among a touch screen, a button, a keyboard, and a dial.

5. The method of claim 1, wherein the trip information comprises one or more from among a trip start time, a trip end time, traffic information, weather conditions, trip duration, trip distance, route elevation changes, route stops, and turns on a route.

6. The method of claim 1, wherein the vehicle dynamics information comprises one or more from among lateral acceleration, longitudinal acceleration, speed, steering information, suspension settings, seat position, and seat orientation.

7. The method of claim 1, wherein the environmental information comprises one or more from among temperature information, humidity information, airflow information, window position information, ambient light information, and odor information.

8. The method of claim 1, wherein determining the probability that the rider suffers from motion sickness is performed based on conditional functions corresponding to ride duration,
   wherein each of the conditional functions comprises a sum of a constant for the ride duration corresponding to the conditional function and a product of one or more functions, and
   wherein the one or more functions include a first function of the rider profile information, the environmental information, the trip information and the vehicle dynamics information, a second function of rider response information, a third function corresponding to a sum of vehicle motion, and a fourth function corresponding to a sum of rider head motion.

9. An apparatus that addresses motion sickness, the apparatus comprising:
    at least one memory comprising computer executable instructions; and
    at least one processor configured to read and execute the computer executable instructions, the computer executable instructions causing the at least one processor to:
    receive rider profile information, trip information, environmental information and vehicle dynamics information wherein the rider profile information includes motion sickness history information of a rider, wherein the motion sickness history information of the rider includes at least one of a count of the times the rider has become motion sick, places where the rider has become motion sick, types of vehicle motion that cause the rider motion sickness, time to first sign of motion sickness, rider's first symptom of motion sickness;
    determine a probability that the rider will suffer from motion sickness during a ride based on the rider profile information, the trip information, the environmental information and the vehicle dynamics information;
    in response to the probability being greater than a predetermined threshold probability corresponding to a rider, adjusting a route to generate an adjusted route to reduce the probability wherein the route is determined in response to the trip information; and
    controlling vehicle movement along the adjusted route.

10. The apparatus of claim 9, wherein the computer executable instructions cause the at least one processor to monitor the rider to determine whether the rider suffers from motion sickness during the ride by receiving the rider response information from one or more from among a camera, a microphone, a biometric sensor, and a user input device.

11. The apparatus of claim 10, wherein the computer executable instructions cause the at least one processor to update the rider profile or the determined probability that the rider will suffer from motion sickness during the ride based on the rider response information, and in response to the updated probability being greater than the predetermined threshold probability corresponding to the rider, perform motion sickness mitigation functions.

12. The apparatus of claim 11, wherein the biometric sensors comprise one or more from among a galvanic skin response sensor, a heart rate sensor, a respiration rate sensor, a skin temperature sensor, blood pressure sensor, and an infrared sensor, wherein the camera comprises one or more from among an in vehicle camera, an infrared camera, and a mobile device camera, wherein the microphone comprises one or more from among a microphone embedded in a vehicle and a microphone of a mobile device, and wherein the user input device comprises one or more from among a touch screen, a button, a keyboard, and a dial.

13. The apparatus of claim 9, wherein the trip information comprises one or more from among a trip start time, a trip end time, traffic information, weather conditions, trip duration, trip distance, route elevation changes, route stops, and turns on a route.

14. The apparatus of claim 9, wherein the vehicle dynamics information comprises one or more from among lateral acceleration, longitudinal acceleration, steering information, suspension settings, seat position, and seat orientation.

15. The apparatus of claim 9, wherein the environmental information comprises one or more from among temperature information, humidity information, airflow information, window position information, ambient light information, and odor information.

16. The apparatus of claim 9, wherein the computer executable instructions cause the at least one processor to determine the probability that the rider suffers from motion sickness based on conditional functions corresponding to ride duration,
    wherein each of the conditional functions comprises a sum of a constant for the ride duration corresponding to the conditional function and a product of one or more functions, and
    wherein the one or more functions include a first function of the rider profile information, the environmental information, the trip information and the vehicle dynamics information, a second function of rider response information, a third function corresponding to a sum of vehicle motion, and a fourth function corresponding to a sum of rider head motion.

17. The apparatus of claim 9, wherein the computer executable instructions cause the at least one processor to the perform motion sickness mitigation functions by performing one or more from among adjusting environmental conditions in a vehicle, outputting displayed images, lights, text, auditory or tactile information configured to assist the rider in mitigating motion sickness, controlling vehicle movement to address motion sickness, providing access to motion sickness medication and remedies, and adjusting a route of a vehicle to address motion sickness.

* * * * *